United States Patent
Kataoka et al.

(10) Patent No.: US 10,479,827 B2
(45) Date of Patent: Nov. 19, 2019

(54) MONOCLONAL ANTIBODY REACTING WITH GLYCOPEPTIDE, AND USE THEREOF

(71) Applicant: SYSMEX CORPORATION, Kobe-shi, Hyogo (JP)

(72) Inventors: Yukiko Kataoka, Tokyo (JP); Tsuyoshi Nomura, Saitama (JP); Koji Fukagawa, Tokyo (JP); Yuriko Egashira, Saitama (JP); Yukiko Higa, Tokyo (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 73 days.

(21) Appl. No.: 15/608,015

(22) Filed: May 30, 2017

(65) Prior Publication Data

US 2017/0342140 A1 Nov. 30, 2017

(30) Foreign Application Priority Data

May 31, 2016 (JP) .................................. 2016-108461
Oct. 17, 2016 (JP) .................................. 2016-203772

(51) Int. Cl.
*C07K 16/18* (2006.01)
*G01N 33/68* (2006.01)
*G01N 33/574* (2006.01)
*C07K 16/30* (2006.01)

(52) U.S. Cl.
CPC ............ *C07K 16/18* (2013.01); *C07K 16/303* (2013.01); *C07K 16/3076* (2013.01); *G01N 33/57488* (2013.01); *G01N 33/689* (2013.01); C07K 2317/14 (2013.01); C07K 2317/33 (2013.01); C07K 2317/34 (2013.01); C07K 2317/565 (2013.01); G01N 2333/471 (2013.01); G01N 2400/02 (2013.01); G01N 2440/38 (2013.01)

(58) Field of Classification Search
CPC .............. C07K 16/303; C07K 16/3076; C07K 2317/34; C07K 2317/41; C07K 2317/565; G01N 2400/02; G01N 2440/38
See application file for complete search history.

(56) References Cited

U.S. PATENT DOCUMENTS

| | | | |
|---|---|---|---|
| 9,383,367 B1 * | 7/2016 | Liu | .................. G01N 33/6878 |
| 2007/0122854 A1 * | 5/2007 | Nam | ................ G01N 33/57419 |
| | | | 435/7.23 |
| 2015/0241450 A1 | 8/2015 | Liu et al. | |

FOREIGN PATENT DOCUMENTS

| | | |
|---|---|---|
| EP | 1 677 112 A1 | 7/2006 |
| JP | 60-067431 A | 4/1985 |
| JP | 63-307900 A | 12/1988 |
| WO | 99/58679 A1 | 11/1999 |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Padlan, Advances in Protein Chemistry, 1996, 49:57-133.*
Berglund et al. (Berglund et al, Protein Science, 2008, 17:606-613.*
Siggins, S., et al., "PLTP secreted by HepG2 cells resembles the high-activity PLTP form in human plasma", Journal of Lipid Research, vol. 44, 2003, pp. 1698-1704 (7 pages).
Siggins, S., et al., "Quantitation of the active and low-active forms of human plasma phospholipid transfer protein by ELISA", Journal of Lipid Research, vol. 45, 2004, pp. 387-395 (9 pages).

* cited by examiner

*Primary Examiner* — Hong Sang
(74) *Attorney, Agent, or Firm* — Sughrue Mion, PLLC

(57) ABSTRACT

Disclosed is a monoclonal antibody reacting with a glycopeptide, wherein the glycopeptide contains a core fucose moiety and at least 4 contiguous amino acid residues that are located on the C-terminal side of a glycosylated asparagine moiety, and both of the core fucose moiety in the glycopeptide and an amino acid residue that is located apart by at least three amino acid residues from the C-terminal of the glycosylated asparagine moiety in the glycopeptide are epitopes for the antibody.

11 Claims, 3 Drawing Sheets
Specification includes a Sequence Listing.

| Length of peptide chain | Length of sugar chain | Structure |
|---|---|---|
| 10 a.a. | 3 | 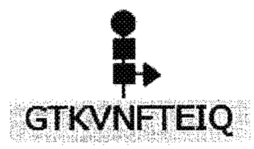 |

| Positive antigen (glycopeptide A) | Negative antigen (non-fucosylated glycopeptide A) |
|---|---|
|  |  |

| Length of peptide chain | Length of sugar chain | Structure |
|---|---|---|
| 7 a.a. | 3 | 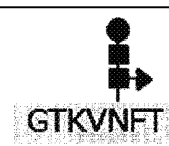  |

SEQUENCE LISTING

<160> NUMBER OF SEQ ID NOS: 25

<210> SEQ ID NO 1

```
<211> LENGTH: 8
<212> TYPE: PRT
<213> ORGANISM: Artificial Sequence
<220> FEATURE:
<223> OTHER INFORMATION: Synthetic CDR-A peptide

<400> SEQUENCE: 1

Gly Phe Asn Ile Lys Asp Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic CDR-A peptide

<400> SEQUENCE: 2

Ile Asp Pro Glu Asp Gly Glu Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic CDR-A peptide

<400> SEQUENCE: 3

Thr Thr Phe Phe Asn
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic CDR-A peptide

<400> SEQUENCE: 4

Lys Ser Leu Leu Tyr Arg Asp Gly Lys Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Synthetic CDR-A peptide

<400> SEQUENCE: 5

Leu Met Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic CDR-A peptide

<400> SEQUENCE: 6

Gln Gln Leu Val Glu Tyr Pro Phe Thr
1               5

<210> SEQ ID NO 7
<211> LENGTH: 8
```

```
<212> TYPE: PRT
<213> ORGANISM: Artificial Sequence
<220> FEATURE:
<223> OTHER INFORMATION: Synthetic CDR-B peptide

<400> SEQUENCE: 7

Gly Phe Asn Ile Asn Asp Tyr Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic CDR-B peptide

<400> SEQUENCE: 8

Ile Asp Pro Glu Asp Gly Glu Thr
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic CDR-B peptide

<400> SEQUENCE: 9

Thr Gly Gly Tyr Phe Val
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic CDR-B peptide

<400> SEQUENCE: 10

Lys Ser Leu Leu Tyr Lys Asp Gly Lys Thr Tyr
1               5                   10

<210> SEQ ID NO 11
<211> LENGTH: 3
<212> TYPE: PRT
<213> ORGANISM: Artificial Sequence
<220> FEATURE:
<223> OTHER INFORMATION: Synthetic CDR-B peptide

<400> SEQUENCE: 11

Leu Met Ser
1

<210> SEQ ID NO 12
<211> LENGTH: 9
<212> TYPE: PRT
<213> ORGANISM: Artificial Sequence
<220> FEATURE:
<223> OTHER INFORMATION: Synthetic CDR-B peptide

<400> SEQUENCE: 12

Gln Gln Leu Val Glu Tyr Pro Phe Thr
1               5

<210> SEQ ID NO 13
<211> LENGTH: 9
<212> TYPE: PRT
```

```
<213> ORGANISM: Artificial Sequence
<220> FEATURE:
<223> OTHER INFORMATION: Synthetic glycopeptide, represented by
      formula(1)
<220> FEATURE:
<221> NAME/KEY: CARBOHYD
<222> LOCATION: (4)..(4)

<400> SEQUENCE: 13

Thr Lys Val Asn Phe Thr Glu Ile Gln
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic glycopeptide, represented by
      formula(2)
<220> FEATURE:
<221> NAME/KEY: CARBOHYD
<222> LOCATION: (4)..(4)

<400> SEQUENCE: 14

Thr Lys Val Asn Phe Thr Glu Ile Gln
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic glycopeptide, represented by
      formula(3)
<220> FEATURE:
<221> NAME/KEY: CARBOHYD
<222> LOCATION: (4)..(4)

<400> SEQUENCE: 15

Thr Lys Val Asn Phe Thr
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic glycopeptide, represented by
      formula(4)
<220> FEATURE:
<221> NAME/KEY: CARBOHYD
<222> LOCATION: (4)..(4)

<400> SEQUENCE: 16

Thr Lys Val Asn Phe Thr
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic glycopeptide, represented by
      formula(5) and (7)
<220> FEATURE:
<221> NAME/KEY: CARBOHYD
<222> LOCATION: (1)..(1)

<400> SEQUENCE: 17

Asn Phe Thr Glu Ile Gln
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic glycopeptide, represented by
      formula(6) and (8)
<220> FEATURE:
<221> NAME/KEY: CARBOHYD
<222> LOCATION: (4)..(4)

<400> SEQUENCE: 18

Thr Lys Val Asn Phe Thr Glu Ile Gln
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic glycopeptide A
<220> FEATURE:
<221> NAME/KEY: CARBOHYD
<222> LOCATION: (5)..(5)

<400> SEQUENCE: 19

Gly Thr Lys Val Asn Phe Thr Glu Ile Gln
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic non-fucosylated glycopeptide A
<220> FEATURE:
<221> NAME/KEY: CARBOHYD
<222> LOCATION: (5)..(5)

<400> SEQUENCE: 20

Gly Thr Lys Val Asn Phe Thr Glu Ile Gln
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic glycopeptide B
<220> FEATURE:
<221> NAME/KEY: CARBOHYD
<222> LOCATION: (5)..(5)

<400> SEQUENCE: 21

Gly Thr Lys Val Asn Phe Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic non-fucosylated glycopeptide B
<220> FEATURE:
<221> NAME/KEY: CARBOHYD
<222> LOCATION: (5)..(5)

<400> SEQUENCE: 22
```

```
Gly Thr Lys Val Asn Phe Thr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide, epitope1
<220> FEATURE:
<221> NAME/KEY: CARBOHYD
<222> LOCATION: (1)..(1)

<400> SEQUENCE: 23

Asn Phe Thr Glu Ile Gln
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide, epitope2
<220> FEATURE:
<221> NAME/KEY: CARBOHYD
<222> LOCATION: (5)..(5)

<400> SEQUENCE: 24

Gly Thr Lys Val Asn Phe Thr Glu Ile Gln
1               5                   10

<210> SEQ ID NO 25
<211> LENGTH: 609
<212> TYPE: PRT
<213> ORGANISM: Homo sapiens
<300> PUBLICATION INFORMATION:
<308> DATABASE ACCESSION NUMBER: NM_001134
<309> DATABASE ENTRY DATE: 2016-09-10
<313> RELEVANT RESIDUES IN SEQ ID NO: (1)..(609)

<400> SEQUENCE: 25

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
                20                  25                  30

Asp Ser Tyr Gln Cys Thr Ala Glu Ile Ser Leu Ala Asp Leu Ala Thr
            35                  40                  45

Ile Phe Phe Ala Gln Phe Val Gln Glu Ala Thr Tyr Lys Glu Val Ser
        50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
                100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
        130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
```

```
            165                 170                 175
Thr Ile Leu Leu Trp Ala Ala Arg Tyr Asp Lys Ile Ile Pro Ser Cys
        180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
        210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
                260                 265                 270

Asp Val Leu Asp Cys Leu Gln Asp Gly Glu Lys Ile Met Ser Tyr Ile
                275                 280                 285

Cys Ser Gln Gln Asp Thr Leu Ser Asn Lys Ile Thr Glu Cys Cys Lys
            290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
                340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
        370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Thr Cys Cys Gln Leu
        450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
            485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
            515                 520                 525

Asp Lys Phe Ile Phe His Lys Asp Leu Cys Gln Ala Gln Gly Val Ala
            530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590
```

```
Ala Glu Glu Gly Gln Lys Leu Ile Ser Lys Thr Arg Ala Ala Leu Gly
            595                 600                 605
Val
```

MONOCLONAL ANTIBODY REACTING WITH GLYCOPEPTIDE, AND USE THEREOF

CROSS REFERENCE TO RELATED APPLICATIONS

This application claims priority from prior Japanese Patent Application Nos. 2016-108461 and 2016-203772, filed on May 31, 2016, entitled "MONOCLONAL ANTIBODY REACTING WITH GLYCOPEPTIDE, AND USE THEREOF", the entire contents of which are incorporated herein by reference.

TECHNICAL FIELD

The present invention relates to a monoclonal antibody reacting with a glycopeptide and a use of the monoclonal antibody.

BACKGROUND

It is believed that, in the transition from hepatitis/liver cirrhosis into liver cancer, the amount of α-fetoprotein (AFP) binding to Lens culinaris agglutinin (LCA) (i.e., LCA-binding AFP) in a biological sample increases. JP S63-307900 describes an antibody for detecting LCA-binding AFP. In JP S63-307900, it is described that an antibody disclosed in this document is reactive with LCA-binding AFP but is unreactive with LCA non-binding AFP.

In JP S63-307900, it is described that LCA-binding AFP contains fucose in the sugar chain moiety thereof. A fraction of AFP binding to Lens culinaris agglutinin in a biological sample is called an "AFP-L3 fraction". The AFP-L3 fraction is composed of fucosylated AFP (i.e., AFP having a structure such that core fucose (i.e., fucose bonding to N-acetylglucosamine (GlcNAc), which is located at a reducing terminal of an N-type sugar chain via an α1-6 bond) is added to an asparagine residue in the AFP).

In the section "Examples" in JP S63-307900, an antibody which binds to LCA-binding AFP (AFP-LCA-R) but does not bind to LCA non-binding AFP (AFP-LCA-NR) is produced (see Example 1, FIGS. 1 and 5). However, an epitope for the antibody is unknown. In the section "Examples", it is concluded that the bindability or non-bindability of the antibody to LCA depends on the presence or absence of fucose, as mentioned above. Therefore, there is a possibility that the bindability of the antibody to an antigen depends on the presence of a fucose moiety in the antigen rather than the sequence for a peptide moiety in the antigen. In this case, the antibody may bind to other fucose-containing proteins non-specifically, as well as AFP. For these reasons, the development of a monoclonal antibody for which the epitopes in a glycopeptide are both of a fucose moiety in the glycopeptide and an amino acid residue contained in a peptide moiety in the glycopeptide has been demanded.

SUMMARY OF THE INVENTION

The scope of the present invention is defined solely by the appended claims, and is not affected to any degree by the statements within this summary.

A first aspect of the present invention provides a monoclonal antibody reacting with a glycopeptide, wherein the glycopeptide contains a core fucose moiety and at least 4 contiguous amino acid residues that are located on the C-terminal side of a glycosylated asparagine moiety, and both of the core fucose moiety in the glycopeptide and an amino acid residue that is located apart by at least three amino acid residues from the C-terminal of the glycosylated asparagine moiety in the glycopeptide are epitopes for the antibody.

A second aspect of the present invention provides a method for producing the above-mentioned antibody, including a step of immunizing an animal with a glycopeptide antigen which contains a core fucose moiety and at least 4 contiguous amino acid residues that are located on the C-terminal side of a glycosylated asparagine moiety.

A third aspect of the present invention provides a method for producing a hybridoma producing the above-mentioned antibody, including a step of immunizing an animal with a glycopeptide antigen which contains a core fucose moiety and at least 4 contiguous amino acid residues that are located on the C-terminal side of a glycosylated asparagine moiety.

A fourth aspect of the present invention provides a monoclonal antibody which reacts with a glycopeptide (SEQ ID NO: 13) represented by formula (1), does not react with a glycopeptide (SEQ ID NO: 14) represented by formula (2), and does not react with a glycopeptide (SEQ ID NO: 15) represented by formula (3).

[Chemical formula 1]

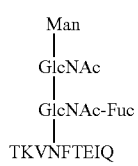

(1)

[Chemical formula 2]

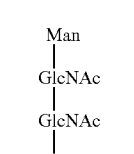

(2)

[Chemical formula 3]

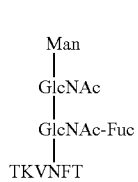

(3)

A fifth aspect of the present invention provides a method for producing the above-mentioned antibody, including a step of immunizing an animal with a glycopeptide antigen (SEQ ID NO: 17) containing a structure represented by formula (5):

[Chemical formula 5]

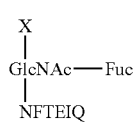

(5)

(wherein X represents an arbitrary sugar chain).

A sixth aspect of the present invention provides a method for producing a hybridoma producing the above-mentioned antibody, including a step of immunizing an animal with a glycopeptide antigen (SEQ ID NO: 17) containing a structure represented by formula (5):

[Chemical formula 5]

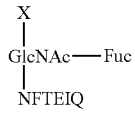
(5)

(wherein X represents an arbitrary sugar chain).

A seventh aspect of the present invention provides a method for measuring fucosylated AFP using the above-mentioned antibody.

A eighth aspect of the present invention provides a fucosylated AFP detection kit including a fucosylated AFP-capturing antibody, a fucosylated AFP-detecting antibody and a solid support, wherein the capturing antibody or the detecting antibody is the above-mentioned antibody.

A ninth aspect of the present invention provides a hybridoma that has been deposited under the international accession No. NITE BP-02263 or NITE BP-02264.

DETAILED DESCRIPTION OF THE PREFERRED EMBODIMENTS

Figure 1:
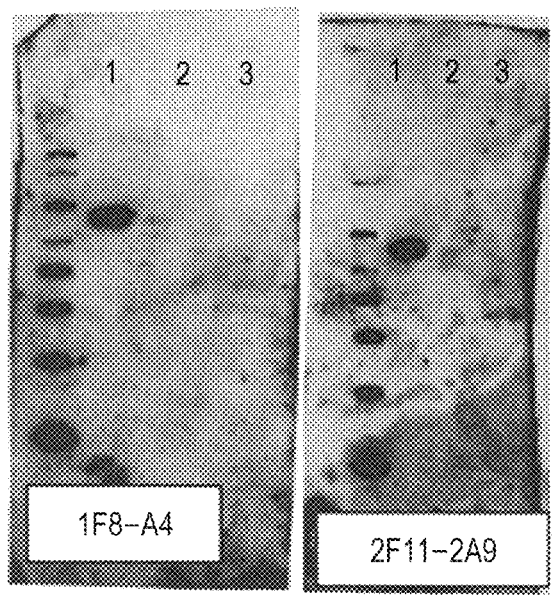
FIG. 1 shows the results of the western blotting of clones 1F8-A4 and 2F11-2A9 both produced in Example 1 (lane 1: fucosylated AFP (AFP-L3/recombinant) (a positive antigen), lane 2: non-fucosylated AFP (a LCA lectin unadsorbed fraction of human serum-originated AFP (LEE biosolutions Inc.)) (a negative antigen), and lane 3: fucosylated ALP (Oriental Yeast Co., ltd./47787055) (a negative antigen)

The antibody according to this embodiment may be any one, as long as the antibody exhibits specificity in a measurement system using a biological sample in which the antibody of this embodiment is used. For example, even when the antibody binds to a substance that is not contained in the biological sample in a non-specific manner, the antibody exhibits the disclosed activity/effect as long as the antibody exhibits specificity under the environment where the antibody of this embodiment is usually used. Specifically, in the case where it is intended to detect a substance contained in a blood sample (e.g., whole blood, serum, plasma) by ELISA, the antibody may be any one as long as the antibody exhibits specificity in an ELISA measurement system, and the antibody may be bound to a substance that is not normally contained in the blood sample or an ELISA reagent.

The antibody of this embodiment is a monoclonal antibody reacting with a glycopeptide, wherein the glycopeptide contains a core fucose moiety and at least 4 contiguous amino acid residues that are located on the C-terminal side of a glycosylated asparagine moiety, and both of the core fucose in the glycopeptide and an amino acid residue that is located apart by at least three amino acid residues from the glycosylated asparagine in the glycopeptide on the C-terminal side of the glycosylated asparagine are epitopes of the antibody.

The glycopeptide to be reacted with the antibody according to this embodiment may be any one, as long as the glycopeptide contains a core fucose moiety and at least 4 contiguous amino acid residues that are located on the C-terminal side of a glycosylated asparagine moiety.

The antibody according to this embodiment is produced by a method involving a step of immunizing an animal with a glycopeptide antigen which contains a core fucose moiety and at least 4 contiguous amino acid residues that are located on the C-terminal side of a glycosylated asparagine moiety.

To the N-terminal of the glycopeptide antigen, a biological polymer (e.g., KLH, BSA) may be bound through PEG or the like. The C-terminal of the glycopeptide antigen may be amidated or the like. The method to be employed for binding the biological polymer to the N-terminal may be any known method. The amidation of the C-terminal may also be carried out by employing any known method.

The step of immunizing an animal with the glycopeptide may be any animal immunizing step employed in any known monoclonal antibody production method. Examples of the monoclonal antibody production method include a mouse spleen method and a mouse iliac lymph node method (see Japanese Patent No. 4098796).

The animal to be immunized is not particularly limited, and the animal may be selected appropriately from non-human animals in accordance with the type of the monoclonal antibody production method to be employed.

Specifically, in the case where a mouse iliac lymph node method is employed as the monoclonal antibody production method, it is possible to conjugate the glycopeptide with a carrier protein (e.g., KLH), then mixing the resultant conjugate with a Freund's adjuvant or the like to prepare an emulsion, and immunizing a mouse at the base of the tail thereof with the glycopeptide solution ((2.5 mg/mL), in terms of a carrier protein content) at least once at a dose of 0.06 mL/mouse.

Subsequent to the immunization of the animal, the production, selection or the like of a hybridoma can be carried out by a known method to produce the antibody according to this embodiment.

In the selection of the hybridoma, the glycopeptide that is used as an antigen, a product which is produced by removing the core fucose moiety from the glycopeptide that is used as an antigen, or a product which has the same sugar chain structure as that of the glycopeptide used as an antigen and has a different peptide chain from that of the glycopeptide used as an antigen may be used as a positive antigen or a negative antigen appropriately. One preferred example of an antigen produced by reducing the number of amino acid residues in the glycopeptide that is used as an antigen is one in which a moiety located on the C-terminal side of the glycopeptide is composed of contiguous 3 residues linked to the glycosylated asparagine moiety.

The criteria of the selection of the hybridoma are as follows. For example, in the case where ELISA is employed, the difference between an OD450 value of a positive antigen and an OD450 value of a negative antigen is 0.05 or more and the OD450 value of the negative antigen is 0.05 or less.

The isotype of the antibody according to this embodiment is not particularly limited. A fragment, such as a peptide containing F(ab')$_2$, Fab', Fab or a CDR, is included within the scope of the antibody according to this embodiment.

The antibody according to this embodiment may be labeled with, for example, biotin or ALP.

The antibody according to this embodiment described above has the above-mentioned properties, and therefore reacts specifically with, for example, a glycoprotein which contains, as partial sequences thereof, a core fucose moiety and at least 4 contiguous amino acid residues that are located on the C-terminal side of a glycosylated asparagine moiety.

The antibody according to this embodiment can be used in ELISA, western blotting, immunohistological staining, immunoprecipitation and the like.

Another monoclonal antibody according to this embodiment specifically reacts with a glycopeptide (SEQ ID NO: 13) represented by formula (1).

[Chemical formula 1]

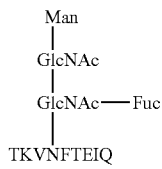

(1)

This monoclonal antibody does not react with a glycopeptide (SEQ ID NO: 14) represented by formula (2), and does not react with a glycopeptide (SEQ ID NO: 15) represented by formula (3), either.

[Chemical formula 2]

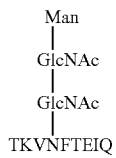

(2)

[Chemical formula 3]

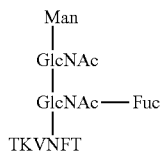

(3)

That is, the antibody according to this embodiment does not react with an antigen that does not have a core fucose moiety and has the amino acid sequence "EIQ" (formula (2)), and does not react with an antigen that has a core fucose moiety and does not have the amino acid sequence "EIQ" (formula (3)), either. In light of these facts, it is considered that the epitope for the antibody according to this embodiment includes both the core fucose moiety and the amino acid sequence "EIQ".

The wording "the antibody according to this embodiment 'reacts with a glycopeptide'" as used herein refers to a matter that the glycopeptide is bound to the antibody through an antigen-antibody reaction.

It is also preferred that the antibody does not react with a glycopeptide (SEQ ID NO: 16) represented by formula (4).

[Chemical formula 4]

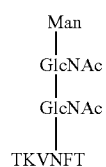

(4)

It is also preferred that the antibody react with fucosylated AFP.

It is also preferred that the antibody can bind to a modified form of fucosylated AFP which is pretreated with a modifier (e.g., SDS) or with heat or the like. In the case where a solution containing SDS is used for the pretreatment, the SDS concentration to be employed for sufficiently modifying fucosylated AFP (wherein the concentration is referred to as a "SDS concentration in pretreatment", hereinafter) is not particularly limited, and is preferably 0.03% by mass (wherein this unit is simply referred to as "%", hereinafter) or more. If the modifier is contained in an excess amount during the antigen-antibody reaction, there is a possibility that the antibody is also modified to cause undesirable influence on the antigen-antibody reaction. In this case, therefore, it is preferred to decrease the concentration of the modifier by dilution or the like. In the case where a solution containing SDS is used as a modifier, the SDS concentration in the antigen-antibody reaction (wherein the concentration is referred to as a "final SDS concentration", hereinafter) is not particularly limited, and is preferably 0.025% or less.

The wording "the antibody according to this embodiment 'reacts with fucosylated AFP'" as used herein refers to a matter that fucosylated AFP is bound to the antibody through an antigen-antibody reaction. The fucosylated AFP may be any one of a recombinant and a naturally occurring substance. One example of the naturally occurring fucosylated AFP is AFP occurring in human blood. The sequence for human AFP has been registered under GenBank Accession No. NM_001134, and has the amino acid sequence represented by SEQ ID NO: 25.

It is also preferred that the antibody react with fucosylated AFP that is modified in the presence of SDS and DTT. The conditions for the modification are as follows: the reaction is carried out at ambient temperature (25° C.) in the presence of 2% of SDS and 50 mM of DTT.

It is also preferred that the antibody does not react with non-fucosylated AFP that is modified in the presence of SDS and DTT. The conditions for the modification are as follows: the reaction is carried out at ambient temperature (25° C.) in the presence of 2% of SDS and 50 mM of DTT.

Examples of the combination of CDRs in the antibody according to this embodiment include CDR-A and CDR-B mentioned below.

<CDR-A> CDRs in a heavy chain respectively contain the amino acid sequence represented by SEQ ID NO: 1, the amino acid sequence represented by SEQ ID NO: 2 and the amino acid sequence represented by SEQ ID NO: 3. CDRs in a light chain respectively contain the amino acid sequence represented by SEQ ID NO: 4, the amino acid sequence represented by SEQ ID NO: 5 and the amino acid sequence represented by SEQ ID NO: 6.

<CDR-B> CDRs in a heavy chain respectively contain the amino acid sequence represented by SEQ ID NO: 7, the amino acid sequence represented by SEQ ID NO: 8 and the amino acid sequence represented by SEQ ID NO: 9. CDRs in a light chain respectively contain the amino acid sequence represented by SEQ ID NO: 10, the amino acid sequence represented by SEQ ID NO: 11 and the amino acid sequence represented by SEQ ID NO: 12.

Hybridomas respectively producing the antibodies according to this embodiment, which respectively have CDR-A and CDR-B as the combination of CDRs, are named "I2-1F8" and "I2-2F11", respectively. These hybridomas have been internationally deposited to the Patent Microorganisms Depositary of the National Institute of Technology and Evaluation (Room 122, 2-5-8, Kazusakamatari, Kisarazu-shi, Chiba 292-0818 Japan) on May 20, 2016, under the accession Nos. NITE BP-02264 and NITE BP-02263, respectively.

The antibody according to this embodiment can be produced by a method including a step of immunizing an animal with a glycopeptide antigen (SEQ ID NO: 17) having a structure represented by formula (5).

[Chemical formula 5]

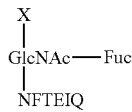

(5)

X represents an arbitrary sugar chain, and is not particularly limited as long as the sugar chain is generally bound to a glycoprotein or a glycopeptide.

The glycopeptide antigen (SEQ ID NO: 18) is more preferably one having the following structure.

[Chemical formula 6]

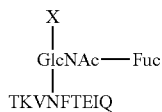

(6)

X represents an arbitrary sugar chain, and is not particularly limited as long as the sugar chain is generally bound to a glycoprotein or a glycopeptide.

To the N-terminal of the glycopeptide antigen, a biological polymer (e.g., KLH) may be bound through PEG or the like. The C-terminal of the glycopeptide antigen may be amidated. The method to be employed for binding the biological polymer to the N-terminal may be any known method. The amidation of the C-terminal may also be carried out employing any known method.

The step to be employed for immunizing an animal with the glycopeptide may be any animal immunizing step employed in the known monoclonal antibody production methods. Examples of the monoclonal antibody production method include a mouse spleen method and a mouse iliac lymph node method (see Japanese Patent No. 4098796).

The animal to be immunized is not particularly limited, and the animal may be selected appropriately from non-human animals in accordance with the type of the monoclonal antibody production method to be employed.

Specifically, in the case where a mouse iliac lymph node method is employed as the monoclonal antibody production method, it is possible to conjugate the glycopeptide with a carrier protein (e.g., KLH), then mixing the resultant conjugate with a Freund's adjuvant or the like to prepare an emulsion, and immunizing a mouse at the base of the tail thereof with the glycopeptide solution ((2.5 mg/mL), in terms of a carrier protein content) at least once at a dose of 0.06 mL/mouse.

Subsequent to the immunization of the animal, the production, selection or the like of a hybridoma can be carried out by any known method to produce the antibody according to this embodiment.

In the selection of the hybridoma, the glycopeptide that is used as an antigen, a product which is produced by removing core fucose from the glycopeptide that is used as an antigen, a product which is produced by reducing the number of amino acid residues in the glycopeptide that is used as an antigen, fucosylated AFP which is modified in the presence of SDS and DTT, non-fucosylated AFP which is modified in the presence of SDS and DTT, a glycopeptide or glycoprotein which has core fucose and has a polypeptide having a different amino acid sequence from that for AFP (e.g., fucosylated ALP) or the like may be used as a positive antigen or a negative antigen appropriately. One preferred example of the product produced by reducing the number of amino acid residues in the glycopeptide that is used as an antigen is one in which the moiety located on the C-terminal side of the glycopeptide is composed of contiguous 3 residues linked to glycosylated asparagine.

The criteria of the selection of the hybridoma are as follows. For example, in the case where ELISA is employed, the difference between an OD450 value of a positive antigen and an OD450 value of a negative antigen is 0.05 or more and the OD450 value of the negative antigen is 0.05 or less.

The isotype of the antibody according to this embodiment is not particularly limited. A fragment, such as a peptide containing F(ab')$_2$, Fab', Fab or a CDR is included within the scope of the antibody according to this embodiment.

The antibody according to this embodiment may be labeled with, for example, biotin or ALP.

The antibody according to this embodiment has the above-mentioned properties, and therefore reacts with fucosylated AFP but does not react with non-fucosylated AFP. Therefore, the antibody according to this embodiment enables the measurement of, for example, fucosylated AFP in a biological sample.

Specific examples of the biological sample include whole blood, serum, plasma and the like collected from a subject. The biological sample may be subjected to a pretreatment such as centrifugation and a modification treatment. The biological sample is preferably subjected to a modification treatment. The conditions for the modification treatment are as follows: the reaction is carried out at ambient temperature (25° C.) in the presence of 2% of SDS and 50 mM of DTT.

In the measurement of fucosylated AFP using the antibody according to this embodiment, any known immunological measurement method can be employed. Examples of the immunological measurement method include an enzyme-linked immunosorbent assay method (an ELISA method), an immune complex transfer immunoassay method (see Japanese Patent Publication Laid-open No. 1-254868), an immuno-nephelometry method, an immunochromatography method and a latex agglutination method. As one example of the measurement step, a case where the fucosylated AFP concentration in a biological sample is measured by a sandwich ELISA method will be described hereinbelow.

First, a complex composed of an antibody for capturing fucosylated AFP in a biological sample (wherein the antibody is also referred to as a "capturing antibody", hereinafter), an antibody for detecting fucosylated AFP (wherein the antibody is also referred to as a "detecting antibody", hereinafter) and fucosylated AFP is formed on a solid phase (also called "solid support"). In the case where fucosylated AFP is contained in the biological sample, the complex can be formed by mixing the biological sample, the capturing antibody and the detecting antibody together. Subsequently, a solution containing the complex is brought into contact with a solid phase that can capture the capturing antibody to form the complex on the solid phase. Alternatively, it may be possible to use a solid phase on which the capturing antibody has been immobilized in advance. That is, a solid phase on which the capturing antibody has been immobilized, the biological sample and the detecting antibody are brought into contact with one another to form the complex on the solid phase. The antibody according to this embodiment can be used as at least one of the capturing antibody and the detecting antibody.

The mode of the immobilization of the capturing antibody onto the solid phase is not particularly limited. For example, the capturing antibody may be bound to the solid phase directly, or the capturing antibody may be bound to the solid phase indirectly through another substance. The direct bonding is, for example, physical adsorption or the like. The indirect bonding is, for example, bonding through a combination of biotin and avidin or streptavidin (also referred to as an "avidin compound", hereinafter). In this case, the capturing antibody and the solid phase may be bound indirectly through a bond between biotin and the avidin compound by modifying the capturing antibody with biotin previously and bonding the avidin compound to the solid phase previously.

The material for the solid phase is not particularly limited, and can be selected from, for example, an organic polymeric compound, an inorganic compound and a biological polymer. Specific examples of the organic polymeric compound include latex, polystyrene and polypropylene. Specific examples of the inorganic compound include a magnetic material (e.g., iron oxide, chromium oxide and ferrite), silica, alumina and glass. Specific examples of the biological polymer include insoluble agarose, insoluble dextran, gelatin and cellulose. Two or more of these materials may be used in combination. The shape of the solid phase is not particularly limited, and examples of the shape include particles, a film, a microplate, a microtube and a test tube.

A fucosylated AFP measurement value in a biological sample can be obtained by detecting the complex formed on the solid phase by any method known in the art. For example, in the case where an antibody labeled with a labeling substance is used as the detecting antibody, the fucosylated AFP measurement value can be obtained by detecting a signal generated from the labeling substance. In the case where a labeled secondary antibody for the detecting antibody is used, the fucosylated AFP measurement value can also be obtained in the same manner.

In this embodiment, it is preferred that fucosylated AFP is pretreated in the above-mentioned manner. In the case where a solution containing SDS is used for the pretreatment, the SDS concentration in pretreatment is not particularly limited and is preferably 0.03% or more. During the antigen-antibody reaction, it is preferred to decrease the concentration of the modifier by dilution, as mentioned above. In the case where a solution containing SDS is used as the modifier, the final SDS concentration is not particularly limited, and is preferably 0.025% or less. In this embodiment, it is preferred to obtain the fucosylated AFP measurement value by carrying out the above-mentioned treatment to cause the reaction of the antibody with the fucosylated AFP.

In this embodiment, it is possible to carry out B/F (Bound/Free) separation for removing any unreacted free component that does not contribute to the formation of the complex, between the complex formation step and the complex detection step. The term "unreacted free component" refers to a component that does not constitute the complex. Examples of the unreacted free component include an antibody that does not bind to fucosylated AFP and a substance other than fucosylated AFP in the biological sample (i.e., a contaminating substance). The means for the B/F separation is not particularly limited. In the case where the solid phase is composed of particles, the B/F separation can be achieved by collecting only the solid phase having the complex captured thereon by centrifugation. In the case where the solid phase is a vessel such as a microplate and a microtube, the B/F separation can be achieved by removing a solution containing the unreacted free component. In the case where the solid phase is composed of magnetic particles, the B/F separation can be achieved by removing a solution containing the unreacted free component by sucking the solution by means of a nozzle while magnetically restraining the magnetic particles with a magnet. After the removal of the unreacted free component, the solid phase having the complex captured thereon may be washed with a proper aqueous medium such as PBS.

The wording "detecting a signal" as used herein refers to all of the qualitative detection of the presence or absence of a signal, the quantification of the intensity of a signal and the semi-quantitative detection of the intensity of a signal. The term "semi-quantitative detection" refers to a matter that the intensity of a signal is rated in accordance with the relative intensity levels, such as "no signal produced", "weak", "medium" and "intense". In this embodiment, it is preferred to detect the intensity of a signal quantitatively or semi-quantitatively.

The labeling substance is not particularly limited, as long as the labeling substance generates a detectable signal. For example, the labeling substance may be a substance that can generate a signal by itself (wherein the substance is also referred to as a "signal-generating substance", hereinafter) or a substance that catalyzes a reaction of another substance to generate a signal. Specific examples of the signal-generating substance include a fluorescent substance and a radioisotope. A specific example of the substance that catalyzes a reaction of another substance to generate a signal is an enzyme. Specific examples of the enzyme include alkaline phosphatase, peroxidase, β-galactosidase and luciferase. Specific examples of the fluorescent substance include a fluorescent dye (e.g., fluorescein isothiocyanate (FITC), rhodamine, Alexa Fluor (registered tradename)) and a fluorescent protein (e.g., GFP). Specific examples of the radio-isotope include $^{125}$I, $^{14}$C and $^{32}$P. Among these labeling substances, an enzyme is preferred, and alkaline phosphatase and peroxidase are particularly preferred.

The method for detecting a signal is known in the art. In this embodiment, the measurement method may be selected appropriately depending on the type of a signal derived from the labeling substance. For example, in the case where the labeling substance is an enzyme, a signal (e.g., light, a color) generated by the reaction of the enzyme with a substrate for the enzyme is measured with a known apparatus such as a spectrophotometer.

The substrate for the enzyme may be selected appropriately from known substrates, depending on the type of the enzyme. For example, in the case where alkaline phosphatase is used as the enzyme, specific examples of the substrate include: a chemiluminescent substrate such as CDP-Star (registered tradename) (disodium 4-chloro-3-(methoxyspiro[1,2-dioxetane-3,2'-(5'-chloro)tricyclo[3.3.1.13,7]decan]-4-yl) phenylphosphate) and CSPD (registered tradename) (disodium 3-(4-methoxyspiro[1,2-dioxetane-3,2-(5'-chloro)tricyclo[3.3.1.13,7]decan]-4-yl)phenyl phosphate); and a chromogenic substrate such as 5-bromo-4-chloro-3-indolylphosphoric acid (BCIP), disodium 5-bromo-6-chloro-indolylphosphate and p-nitrophenylphosphoric acid. In the case where peroxidase is used as the enzyme, specific examples of the substrate include: a chemiluminescent substrate such as luminol and derivatives thereof; and a chromogenic substrate such as ammonium 2,2'-azinobis(3-ethylbenzothiazoline-6-sulfonate) (ABTS), 1,2-phenylenediamine (OPD) and 3,3',5,5'-tetramethylbenzidine (TMB).

In the case where the labeling substance is a radioisotope, a radioactive ray can be measured as the signal, using a known apparatus such as a scintillation counter. In the case where the labeling substance is a fluorescent substance, fluorescence can be measured as the signal, using a known apparatus such as a fluorescence microplate reader. An excitation wavelength and a fluorescence wavelength can be determined appropriately depending on the type of the fluorescent substance used.

The result of the detection of the signal may be employed as a fucosylated AFP measurement value. For example, in the case where the intensity of the signal is detected quantitatively, a measurement value of the signal intensity or a value obtained from the measurement value may be employed as the fucosylated AFP measurement value. An example of the value obtained from a measurement value of the intensity of the signal is a value that is obtained by subtracting a measurement value of a negative control sample or a value of background from a fucosylated AFP measurement value. The negative control sample may be selected appropriately, and is a biological sample collected from a normal person or the like.

In this embodiment, it is possible to obtain fucosylated AFP measurement values from multiple standard samples in each of which the fucosylated AFP concentration is known, and then produce a calibration curve that shows the relationship between the fucosylated AFP concentrations and the fucosylated AFP measurement values. A value of the fucosylated AFP concentration in the biological sample can be obtained by applying a fucosylated AFP measurement value obtained from the biological sample to the calibration curve.

In this embodiment, the fucosylated AFP concentration in a biological sample may be measured by a sandwich ELISA method using the capturing antibody immobilized onto magnetic particles and the detecting antibody labeled with the labeling substance. In this case, the measurement may be carried out using a commercially available fully automatic immunoassay apparatus such as an apparatus of a HISCL series (manufactured by Sysmex Corporation).

The antibody according to this embodiment can be used in a fucosylated AFP detection kit. The fucosylated AFP detection kit according to this embodiment contains a capturing antibody, a detecting antibody and a solid phase. The antibody according to this embodiment can be used as the capturing antibody or the detecting antibody. In a sandwich immunoassay, the antibody according to this embodiment can be used as either one of the capturing antibody and the detecting antibody.

In the case where the labeling substance for the detecting antibody is an enzyme, the fucosylated AFP detection kit according to this embodiment may additionally contain a substrate for the enzyme. The form of each of the labeling substance and the substrate is not particularly limited, and may be a solid form (e.g., a powder, a crystal, a lyophilized product) or a liquid form (e.g., a solution, a suspension, an emulsion).

The fucosylated AFP detection kit according to this embodiment may additionally contain a pretreatment reagent containing 0.03% or more of SDS, for the purpose of pretreating the above-mentioned fucosylated AFP. The reagent is the same as the above-mentioned solution containing 0.03% or more of SDS.

The fucosylated AFP detection kit according to this embodiment may additionally contain a pretreated solution of a biological sample, a washing solution for the solid phase, an enzymatic reaction terminator, a calibrator and the like as required.

In the fucosylated AFP detection kit according to this embodiment, the capturing antibody, the detecting antibody, the solid phase and others may be enclosed in a container or may be packed separately, in accordance with the form of the kit. In the fucosylated AFP detection kit according to this embodiment, the capturing antibody may be bound to the solid phase directly, or the capturing antibody and the solid phase may be bound to each other indirectly through another substance. In the kit according to this embodiment, in the case where the capturing antibody and the solid phase are bound to each other indirectly, the capturing antibody and the solid phase may be enclosed in different containers. For example, in the case where the capturing antibody and the solid phase are bound to each other indirectly through biotin and an avidin compound, it is possible to enclose the capturing antibody modified with the biotin in one container and the solid phase having the avidin compound bound thereto is enclosed in another container. The details about the biological sample, the capturing antibody, the detecting antibody, the solid phase and others are as mentioned above in the section relating to the measurement method.

Fucosylated AFP is known to be involved in liver cancer. Therefore, the fucosylated AFP detection kit according to this embodiment can be used for the diagnosis of liver cancer.

EXAMPLES

Hereinbelow, the present invention will be described in more detail by way of examples. However, the present invention is not limited by these examples in any way.

Example 1

Acquisition of Antibody:
(1) Acquisition of Antibodies

Figure 5:
FIG. 5 shows a glycopeptide A structure.

Hybridomas producing antibodies were produced by a mouse iliac lymph node method (Japanese Patent No. 4098796). Specifically, the production of the hybridomas was carried out in the following manner: a glycopeptide A (SEQ ID NO: 19) having the structure shown in FIG. 5 was synthesized, then the glycopeptide A was conjugated with KLH, and then an emulsion, which was prepared by mixing the resultant conjugate with Freund's complete adjuvant so as to adjust the concentration of the conjugate in the emulsion to 2.5 mg/mL (in terms of carrier protein content), was injected once to the base of the tail of each of mice at a dose of 0.06 mL/mouse. Seventeen days after the immunization, a 2.5-mg/mL (in terms of carrier protein content) KLH-conjugated glycopeptide A solution was injected once to the base of the tail of each of the mice at a dose of 0.06 mL/mouse to boost the immunity of the mice. Four days after the immunity boosting, lymphocytes were isolated from the iliac lymph node of each of the mice, and then each of the lymphocytes was cell-fused to a myeloma. In this manner, the hybridomas were produced.

In the structure, a filled circle represents a mannose molecule, a filled square represents a N-acetylglucosamine molecule and a filled triangle represents a fucose molecule. The N-terminal of the glycopeptide is KLH-PEG4, and the C-terminal of the glycopeptide is amidated.

(2) Primary Screening

Figure 6:
FIG. 6 shows glycopeptide A and non-fucosylated glycopeptide A structures.
Figure 6:

The hybridomas produced in item (1) were subjected to antigen solid-phase ELISA using a positive antigen (a glycopeptide A) or a negative antigen (a non-fucosylated glycopeptide A: SEQ ID NO: 20) both shown in FIG. 6, and wells in each of which the reaction with the positive antigen was observed but the reaction with the negative antigen was observed to a lesser extent were selected from the hybridomas. The antigen solid-phase ELISA was carried out in the following manner. The results are shown in Table 3.

In each of the structures, a filled circle represents a mannose molecule, a filled square represents a N-acetylglucosamine molecule and a filled triangle represents a fucose molecule. The N-terminal of each of the glycopeptides is BSA-PEG4, and the C-terminal of each of the glycopeptides is amidated.

<Protocol>

(1) Each of the screening antigens (1 μg/ml (a diluent: a 10-mM phosphate buffer, pH 7)) was added to a 96-well plate (nunc Maxisoap/446612) in a volume of 50 μl/well, and was then incubated at 37° C. for 1 hr to immobilize each of the antigens.

(2) The wells were washed with 300 μl/well of PBST five times.

(3) The wells were blocked overnight at 4° C. with 100 μl/well of 1% BSA-PBS.

(4) The wells were washed with 300 μl/well of PBST five times.

(5) An antibody culture supernatant (a primary antibody) was 10-fold diluted with 1% BSA-PBS, then the resultant dilution was added to the wells in a volume of 50 μl/well, and then the resultant mixture was reacted at room temperature (also referred to as "RT", hereinafter) for 1 hr.

(6) The wells were washed with 300 μl/well of PBST five times.

(7) Anti-mouse IgG-HRP (JR/715-035-151) and anti-mouse IgG L-chain-HRP (JIR/115-035-174) were separately 20,000-fold diluted with 1% BSA-PBS, then each of the resultant dilutions was added to the wells in a volume of 50 μl/well, and then the resultant mixture was reacted at RT for 0.5 hr.

(8) The wells were washed with 300 μl/well of PBST five times.

(9) A HRP chromogenic substrate was added to the wells in a volume of 100 μl/well to develop a color.

(10) A stop solution was added to the wells in a volume of 100 μl/well to terminate the development of the color.

(11) OD450 values of the wells were measured.

(12) Seven wells in each of which the difference between the intensity of a signal for the positive antigen and the intensity of a signal for the negative antigen was large and the reaction with the negative antigen occurred to a lesser extent were selected for the secondary screening.

TABLE 3

| Number of wells | Positive antigen (glycopeptide A) (OD450 > 0.1 was determined "+") | Negative antigen (non-fucosylated glycopeptide A) (OD450 > 0.05 was determined "+") | Number of positive wells |
| --- | --- | --- | --- |
| 384 | − | − | 149 |
|  | − | + | 16 |
|  | + | + | 215 |
|  | + | − | 4 |

(3) Secondary Screening

Wells in each of which both of core fucose and an amino acid were recognized were selected from the wells obtained in step (2) by western blotting using each of the antigens shown below, and were then subjected to cloning. The western blotting was carried out in the following manner.

<Materials>

Screening antigens:
Positive antigen: fucosylated AFP (AFP-L3/recombinant)
Negative antigen 1: non-fucosylated AFP (a LCA lectin unadsorbed fraction of human serum-originated AFP (LEE bio solutions Inc.))
Negative antigen 2: fucosylated ALP (Oriental Yeast Co., ltd./47787055)
Primary antibodies:
Screening antibody: a primary-screening-positive culture supernatant
Negative control: a hybridoma culture medium
Secondary antibodies:
Anti-mouse-IgG(Fc) Ab-HRP (BET/A90-131P)
Anti-mouse-IgM Ab-HRP (SBA/1020-05)
Blocking agent: PVDF Blocking Reagent for Can Get Signal (TOYOBO/NYPBR01)
Washing solution: TBST
Diluent: 1% BSA-TBST
PVDF membrane: (iBlot (registered tradename) 2 Transfer Stacks, PVDF, mini/IB24002)
Blotting apparatus: (iBlot2)
Luminescence detection reagent: ECL prime Western Blotting Detection Reagent (GE Health Care/RPN2232)

<Protocol>

(1) NuPAGE LDS Sample Buffer (4×) (Thermo/NP0008) and NuPAGE Sample Reducing Agent (10×) (Thermo/NP0009) were added to and mixed with each of the screening antigens in amounts of fourth part and tenth part, respectively, of the amount of each of the screening antigens.

(2) A molecular weight marker and each of the screening antigens shown in (1) were subjected to electrophoresis (SDS-PAGE) at an antigen amount shown below. Lane 0: a molecular weight marker (MagicMark (registered tradename) XP Western Protein Standard/LC5602), lane 1: a positive antigen: fucosylated AFP (AFP-L3) 50 ng, lane 2:

a negative antigen 1: non-fucosylated AFP 50 ng, and lane 3: a negative antigen 2: fucosylated ALP 50 ng (3) Blotting on a PVDF membrane was carried out.

(4) The membrane was immersed in PVDF Blocking Reagent for Can Get Signal at RT for 1 hr to block the blotting.

(5) The membrane was washed with TBST three times.

(6) The primary antibodies were diluted with 1% BSA-TBST at dilution ratios shown below and were then reacted at 4° C. overnight.

Screening antibody: a 1$^{st}$ screening-positive culture supernatant, a 10-fold dilution.

Negative control: a hybridoma culture medium, a 10-fold dilution.

(7) The membrane was washed with TBST three times.

(8) Secondary antibodies (a mixture of two types of antibodies) were diluted with 1% BSA-TBST at the dilution ratios mentioned below, and then were reacted at RT for 1 hr.

Anti-mouse-IgG(Fc) Ab-HRP: a 20,000-fold dilution.
Anti-mouse-IgM Ab-HRP: a 5,000-fold dilution.

(9) The membrane was washed with TBST three times.

(10) The chemiluminescent detection was carried out.

(11) Five wells in each of which a band of only the positive antigen was detected were determined as "positive", and were then subjected to cloning.

(4) Cloning

Cells in each of the five wells that were selected in item (3) were cloned by a limiting dilution method. Each of culture supernatants was screened again in the same manner as in the primary screening mentioned in item (2). In this manner, two types of clones were obtained. The ELISA data of the clones are shown in Table 4.

TABLE 4

| Name of clone | Positive antigen (glycopeptide A) | Negative antigen (non-fucosylated glycopeptide A) |
|---|---|---|
| 1F8-A4 | 0.332 | 0.030 |
| 2F11-2A9 | 0.442 | 0.009 |

Each of culture supernatants of the two types of clones was subjected to western blotting in the same manner as in the secondary screening mentioned in item (3). As a result, it was confirmed that the two types of clones reacted with AFP-L3 specifically. The results of the western blotting are shown in FIG. 1. In FIG. 1, the antigens used in the individual lanes are as follows: lane 1: fucosylated AFP (AFP-L3/recombinant) (a positive antigen); lane 2: non-fucosylated AFP (a LCA lectin unadsorbed fraction of human serum-originated AFP (LEE biosolutions Inc.)) (a negative antigen); and lane 3: fucosylated ALP (Oriental Yeast Co., ltd./47787055) (a negative antigen).

(5) Confirmation of Epitopes

Figure 7:
FIG. 7 shows glycopeptide B and non-fucosylated glycopeptide B structures.
Figure 7:
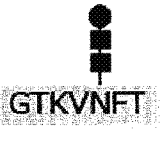

In order to confirm epitopes for an antibody produced from each of the clones, it was confirmed whether or not the antibody was able to recognize a glycopeptide B (SEQ ID NO: 21) and a non-fucosylated glycopeptide B (SEQ ID NO: 22) shown in FIG. 7, in each of which the number of amino acid residues was smaller than that in the sequence for the glycopeptide A that was used as an immunogen, in the same manner as in item (2). The results are shown in Table 6. AAL lectin that recognizes fucose was used as a positive control (PC) for the glycopeptide B, and WGA lectin that recognizes GlcNAc was used as a positive control for the non-fucosylated glycopeptide B. As a negative control (NC), a buffer solution was used.

In the structures, a filled circle represents a mannose molecule, a filled square represents a N-acetylglucosamine molecule and a filled triangle represents a fucose molecule. The N-terminal of each of the glycopeptides is BSA-PEG4, and the C-terminal of each of the glycopeptides is amidated.

TABLE 6

| Name of clone | Glycopeptide B | Non-fucosylated glycopeptide B |
|---|---|---|
| 1F8-A4 | 0.048 | 0.043 |
| 2F11-2A9 | 0.046 | 0.049 |
| PC | 0.335 | 3.0 |
| NC | 0.044 | 0.044 |

All of the antibodies reacted with the glycopeptide A antigen but did not react with the glycopeptide B antigen. From this results, it was found that the sequence for an epitope for each of the antibodies was a region containing at least either one of the sequences shown in Table 7.

TABLE 7

| Epitope sequence 1 (SEQ ID NO: 23) | Epitope sequence 2 (SEQ ID NO: 24) |
|---|---|
| Man<br>\|<br>GlcNAc<br>\|<br>GlcNAc—Fuc<br>\|<br>NFTEIQ | Man<br>\|<br>GlcNAc<br>\|<br>GlcNAc—Fuc<br>\|<br>GTKVNFTEIQ |

(6) Confirmation of Sequences for CDR Sequences

With respect to the five clones produced in item (4), CDRs in the antibodies were analyzed. As a result, it was found that there were two patterns of CDR sequences below. The sequences (SEQ ID NOs: 1 to 6) for the CDRs in an antibody produced from 1F8-A4 are shown in Table 8. The sequences (SEQ ID NOs: 7 to 12) for the CDRs in an antibody produced from 2F11-2A9 are shown in Table 9.

TABLE 8

|  | Heavy chain | Light chain |
|---|---|---|
| CDR1 | GFNIKDYY | KSLLYRDGKTY |
| CDR2 | IDPEDGES | LMS |
| CDR3 | TTFFN | QQLVEYPFT |

TABLE 9

|  | Heavy chain | Light chain |
|---|---|---|
| CDR1 | GFNINDYF | KSLLYKDGKTY |
| CDR2 | IDPEDGET | LMS |
| CDR3 | TGGYFV | QQLVEYPFT |

Among the clones produced above, 1F8-A4 was named "I2-1F8" and has been internationally deposited (NITE BP-02264), and 2F11-2A9 was named "I2-2F11" and has been internationally deposited (NITE BP-02263).

Example 2

Construction of sandwich ELISA, and influence of SDS on reactivity

The detection by sandwich ELISA was carried out using each of I2-1F8 and I2-2F11 produced in Example 1 in the following manner. The influence of SDS on reactivity was examined.

<Materials>

Antibody sensitization plate (I2-1F8, I2-2F11/2.5 µg/mL, 100 µL/well)

Recombinant AFP-L3 antigen

Anti-AFP antibody: a polyclonal antibody to Alpha-Fetoprotein (WLS/# PAA153Hu01)

Labeled antibody: Goat anti-rabbit immunoglobulin-HRP

Buffer A: 150 mM NaCl+1% BSA/a 10-mM phosphate buffer solution (pH 7)

Buffer B: 150 mM NaCl+0.05% Tween20/a 10-mM phosphate buffer solution (pH 7)

<Protocol>

(1) (An antigen pretreatment) Each of SDS solutions having concentrations of 2%, 1%, 0.5%, 0.25%, 0.13% and 0.06%, respectively, was added to a 20-µg/mL AFP-L3 antigen solution in the equal volumes to each other, and the resultant solution was mixed and was then allowed to leave for 3 minutes or longer. (SDS concentration in pretreatment: 0.03 to 1%)

(2) The solution was diluted with Buffer A in such a manner that the antigen concentration in the solution became 1 µg/mL, 0.5 µg/mL or 0.25 µg/mL. (Final SDS concentration: 0.00075% to 0.1%)

(3) The resultant antigen solution was added in a volume of 100 µL/well to the antibody sensitization plate and was reacted at RT for 60 minutes.

(4) The wells were washed with Buffer B, then an anti-AFP antibody that was diluted at a dilution ratio of 400 folds was added to the wells in a volume of 100 µL/well, and the resultant solution was reacted at RT for 60 minutes.

(5) The wells were washed with Buffer B, then a labeled antibody that was diluted at a dilution ratio of 4000 folds was added to the wells in a volume of 100 µL/well, and the resultant solution was reacted at RT for 40 minutes.

(6) The wells were washed with Buffer B, and then a HRP chromogenic substrate was added to the well in a volume of 100 µl/well to develop a color for 20 minutes.

(7) A stop solution was added to the wells in a volume of 100 µl/well to terminate the development of the color, and then an OD450 value in each of the wells was measured.

<Results>

The OD450 measurement values which were measured using I2-1F8 at various antigen concentrations, various final SDS concentrations and various SDS concentrations in pretreatment are shown in Table 10. The OD450 measurement values which were measured using I2-2F11 at various antigen concentrations, various final SDS concentrations and various SDS concentrations in pretreatment are shown in Table 11.

TABLE 10

| Final SDS concentration | Antigen: 1 µg/mL | | Antigen: 0.5 µg/mL | | Antigen: 0.25 µg/mL | |
|---|---|---|---|---|---|---|
| | SDS concentration in pretreatment | OD450 | SDS concentration in pretreatment | OD450 | SDS concentration in pretreatment | OD450 |
| 0.1% | 1% | 0.09 | — | — | — | — |
| 0.05% | 0.5% | 0.08 | 1% | 0.08 | — | — |
| 0.025% | 0.25% | 0.08 | 0.5% | 0.08 | 1% | 0.08 |
| 0.013% | 0.125% | 0.34 | 0.25% | 0.26 | 0.5% | 0.17 |
| 0.006% | 0.06% | 0.34 | 0.125% | 0.23 | 0.25% | 0.16 |
| 0.003% | 0.03% | 0.36 | 0.06% | 0.21 | 0.125% | 0.15 |
| 0.0015% | — | — | 0.03% | 0.24 | 0.06% | 0.14 |
| 0.00075% | — | — | — | — | 0.03% | 0.15 |

TABLE 11

| Final SDS concentration | Antigen: 1 µg/mL | | Antigen: 0.5 µg/mL | | Antigen: 0.25 µg/mL | |
|---|---|---|---|---|---|---|
| | SDS concentration in pretreatment | OD450 | SDS concentration in pretreatment | OD450 | SDS concentration in pretreatment | OD450 |
| 0.1% | 1% | 0.65 | — | — | — | — |
| 0.05% | 0.5% | 1.09 | 1% | 0.90 | — | — |
| 0.025% | 0.25% | 2.17 | 0.5% | 1.62 | 1% | 0.80 |
| 0.013% | 0.125% | 2.22 | 0.25% | 1.58 | 0.5% | 0.77 |
| 0.006% | 0.06% | 2.13 | 0.125% | 1.58 | 0.25% | 0.75 |
| 0.003% | 0.03% | 2.12 | 0.06% | 1.52 | 0.125% | 0.76 |
| 0.0015% | — | — | 0.03% | 1.47 | 0.06% | 0.74 |
| 0.00075% | — | — | — | — | 0.03% | 0.73 |

When I2-1F8 was used, signals were increased in an antigen concentration-dependent manner at final SDS concentrations of 0.013% or less. When I2-2F11 was used, signals were increased in an antigen concentration-dependent manner at final SDS concentrations of 0.025% or less.

Example 3

Confirmation of specificity of sandwich ELISA

The specificity of the sandwich ELISA constructed in Example 2 was confirmed in the following manner.

<Materials>

Antibody sensitization plate (I2-1F8, I2-2F11/2.5 µg/mL, 100 µL/well)

Positive antigen: recombinant AFP-L3 antigen

Negative antigen 1: non-fucosylated AFP (an LCA lectin unadsorbed fraction of human serum-originated AFP (LEE biosolutions Inc.))

Negative antigen 2: a fucosylated protein ALP other than AFP (Oriental Yeast Co., ltd.)

Biotinylated anti-AFP antibody: anti-AFP, Human (mouse) (ABV/H00000174-M01)

Detection reagent: HRP-Conjugated Streptavidin (Thermo/N100)

Buffer A: 150 mM NaCl+1% BSA/a 10-mM phosphate buffer solution (pH 7)

Buffer B: 150 mM NaCl+0.05% Tween20/a 10-mM phosphate buffer solution (pH 7)

<Protocol>

(1) A 0.06% SDS solution was added to a 20-µg/mL solution of each of the antigens (to modify the antigens) or was not added to the solution (not to modify the antigens) in the equal volumes to each other, and the resultant solution was mixed and was then allowed to leave for 3 minutes or longer. (SDS concentration in pretreatment: 0.03%)

(2) The solution was diluted with Buffer A in such a manner that the antigen concentration became 1000 ng/mL, 500 ng/mL, 250 ng/mL, 125 ng/mL, 63 ng/mL or 31 ng/mL.

(3) Each of the antigen solutions was added to an antibody sensitization plate in a volume of 100 µL/well, and the resultant solution was reacted at RT for 60 minutes.

(4) The wells were washed with Buffer B, and a biotinylated anti-AFP antibody that was diluted at a dilution ratio of 480 folds was added to the wells in a volume of 100 µL/well, and then the resultant solution was reacted at RT for 60 minutes.

(5) The wells were washed with Buffer B, and then a detection reagent that was diluted at a dilution ratio of 10000 folds was added to the wells in a volume of 100 µL/well, and then the resultant solution was reacted at RT for 60 minutes.

(6) The wells were washed with Buffer B, and then a HRP chromogenic substrate was added to the wells in a volume of 100 µl/well to develop a color for 10 minutes.

Figure 2:
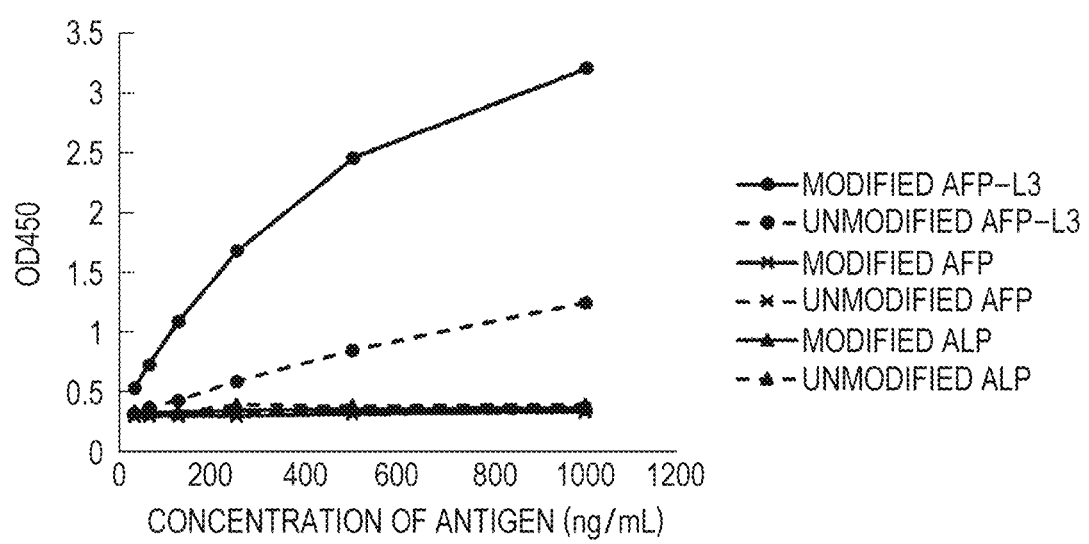
FIG. 2 shows the measurement values of OD450 at various antigen concentrations using clone I2-1F8 that is produced in Example 1.
Figure 3:
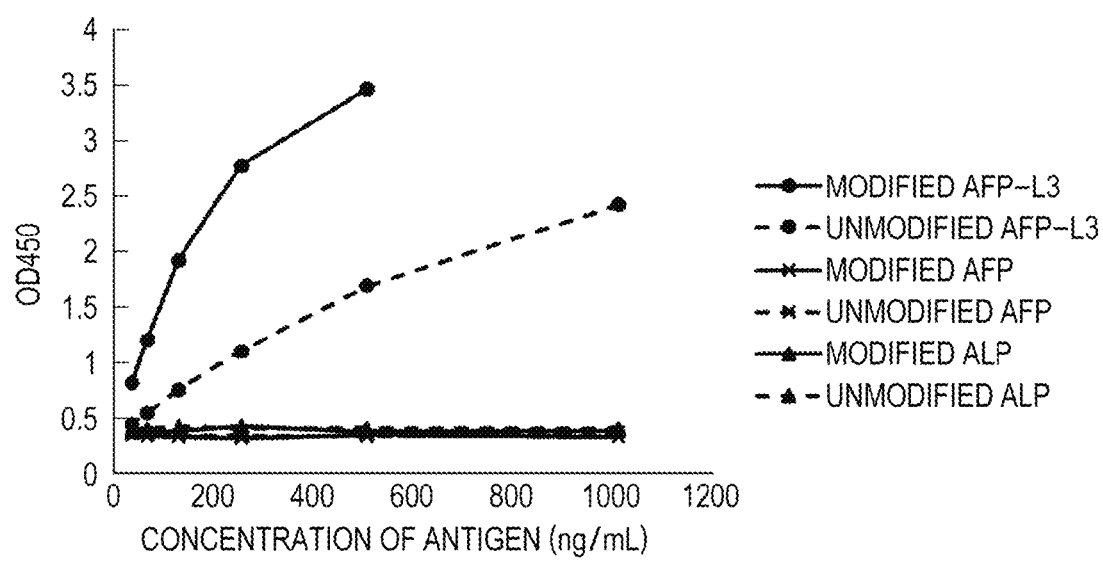
FIG. 3 shows OD450 measurement values which are measured at various antigen concentrations using a clone I2-2F11 that is produced in Example 1.

(7) A stop solution was added to the wells in a volume of 100 μl/well to terminate the development of the color, and then an OD450 value of the solution in each of the wells was measured.
<Results>
The OD450 measurement values which were measured using I2-1F8 at various antigen concentrations are shown in Table 12 and FIG. 2. The OD450 measurement values which were measured using I2-2F11 at various antigen concentrations are shown in Table 13 and FIG. 3.

TABLE 12

| Antigen concentration (ng/mL) | 1000 | 500 | 250 | 125 | 63 | 31 |
|---|---|---|---|---|---|---|
| Modified AFP-L3 | 3.21 | 2.46 | 1.68 | 1.08 | 0.72 | 0.52 |
| Unmodified AFP-L3 | 1.24 | 0.84 | 0.58 | 0.42 | 0.36 | 0.32 |
| Modified AFP | 0.33 | 0.31 | 0.29 | 0.29 | 0.29 | 0.29 |
| Unmodified AFP | 0.36 | 0.33 | 0.32 | 0.30 | 0.30 | 0.29 |
| Modified ALP | 0.36 | 0.35 | 0.34 | 0.32 | 0.32 | 0.33 |
| Unmodified ALP | 0.39 | 0.38 | 0.39 | 0.32 | 0.32 | 0.34 |

TABLE 13

| Antigen concentration (ng/mL) | 1000 | 500 | 250 | 125 | 63 | 31 |
|---|---|---|---|---|---|---|
| Modified AFP-L3 | — | 3.44 | 2.76 | 1.91 | 1.20 | 0.82 |
| Unmodified AFP-L3 | 2.39 | 1.68 | 1.10 | 0.76 | 0.55 | 0.45 |
| Modified AFP | 0.33 | 0.35 | 0.33 | 0.34 | 0.35 | 0.37 |
| Unmodified AFP | 0.37 | 0.34 | 0.35 | 0.35 | 0.37 | 0.36 |
| Modified ALP | 0.38 | 0.38 | 0.43 | 0.39 | 0.38 | 0.38 |
| Unmodified ALP | 0.40 | 0.41 | 0.41 | 0.43 | 0.41 | 0.41 |

Both of I2-1F8 and I2-2F11 did not react with non-fucosylated AFP or ALP regardless of whether the antigens were modified or unmodified. In contrast, both of I2-1F8 and I2-2F11 reacted with AFP-L3 and showed the increase in signal intensities in an antigen concentration-dependent manner. Particularly I2-1F8 and I2-2F11 showed significantly improved reactivity with modified AFP-L3. From these results, it was demonstrated that the specific reaction of each of I2-1F8 and I2-2F11 with AFP-L3 in sandwich ELISA was achieved through the simultaneous recognition of the fucose moiety and the peptide moiety in AFP-L3. It was also demonstrated that both of I2-1F8 and I2-2F11 reacted with the antigens more strongly when the antigens were pretreated with 0.03% of SDS.

Example 4

Figure 4:
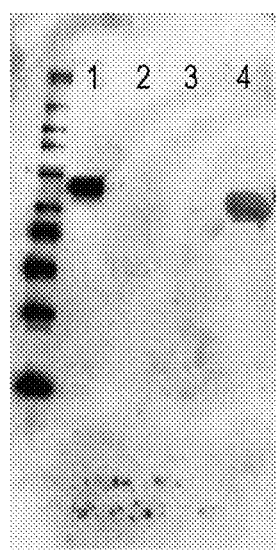
FIG. 4 shows the results of the western blotting of a clone I2-1F8 that is produced in Example 1 (lane 1: recombinant AFP-L3, lane 2: non-fucosylated AFP, lane 3: naturally occurring human AFP (μ-TAS Wako, calibrator 1 for AFP-L3), and lane 4: naturally occurring human AFP-L3 (μ-TAS Wako, calibrator 2 for AFP-L3))

Reactivity with naturally occurring human AFP-L3
Western blotting was carried out in the following manner to determine whether or not I2-1F8 reacted with naturally occurring human AFP-L3.
<Materials>
Primary antibody: I2-1F8 (a 10-fold dilution of a hybridoma culture supernatant), at 4° C. O/N
Secondary antibody: anti-mouse-IgG(Fc) Ab-HRP (BET/#A90-131P) (a 20,000-fold dilution), at RT for 1 hr <Protocol>
Western blotting was carried out in the same manner as in Example 1 (3), except that the above-mentioned primary antibody and secondary antibody were used instead.
<Results>
The results of the western blotting are shown in FIG. 4. I2-1F8 also reacted with naturally occurring human AFP-L3. In FIG. 4, the antigens in the individual lanes are as follows: lane 1: recombinant AFP-L3, lane 2: non-fucosylated AFP, lane 3: naturally occurring human AFP (calibrator 1 for μ-TAS Wako AFP-L3), and lane 4: naturally occurring human AFP-L3 (calibrator 2 for μ-TAS Wako AFP-L3)

Example 5

Influence of SDS on reactivity
The influence of SDS on reactivity was examined employing the ELISA constructed in Example 2.
<Materials>
The same materials as those used in Example 2 were used, except that I2-1F8 was used as antibody.
<Protocol>
(1) (Pretreatment of antigen) Each of SDS solutions respectively having concentrations of 0.031%, 0.016%, 0.008% and 0.004% was added to a 20-μg/mL AFP-L3 antigen solution in equal volumes to each other, and the resultant solution was mixed and was then allowed to leave for 3 minutes or longer.
(2) The solution was diluted with Buffer A in such a manner that the antigen concentration became 0.4 μg/mL, 0.2 μg/mL or 0.1 μg/mL. (Final SDS concentration: 0.00032 to 0.00001%)
(3) The subsequent procedures were carried out in the same manner as in Example 2.
<Results>
The OD450 measurement values which were measured using I2-1F8 at various antigen concentrations, various final SDS concentrations and various SDS concentrations in pretreatment are shown in Table 14.

TABLE 14

| | Antigen: 0.4 μg/mL | | Antigen: 0.2 μg/mL | | Antigen: 0.1 μg/mL | |
|---|---|---|---|---|---|---|
| Final SDS concentration ($\times 10^{-3}$) | SDS concentration in pretreatment | OD450 | SDS concentration in pretreatment | OD450 | SDS concentration in pretreatment | OD450 |
| 0.32% | 0.016% | 0.67 | — | — | — | — |
| 0.16% | 0.008% | 0.49 | 0.016% | 0.46 | — | — |
| 0.08% | 0.004% | 0.42 | 0.008% | 0.32 | 0.016% | 0.33 |
| 0.04% | 0.002% | 0.34 | 0.004% | 0.29 | 0.008% | 0.25 |
| 0.02% | — | — | 0.002% | 0.26 | 0.004% | 0.24 |
| 0.01% | — | — | — | — | 0.002% | 0.23 |
| 0% | 0% | 0.32 | 0% | 0.25 | 0% | 0.22 |

Signals were detected in a concentration-dependent manner even when the SDS concentrations in pretreatment were 0.016% or less.

What is claimed is:

1. A monoclonal antibody, which reacts with a glycopeptide of formula (1) (SEQ ID NO: 13), does not react with a glycopeptide of formula (2) (SEQ ID NO: 14), and does not react with a glycopeptide of formula (3) (SEQ ID NO: 15):

[Chemical formula 1]

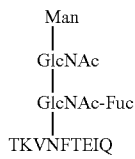
(1)

[Chemical formula 2]

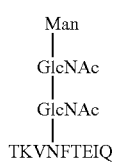
(2)

[Chemical formula 3]

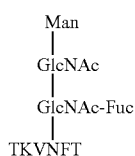
(3)

wherein said antibody comprises a heavy chain comprising three complementarity-determining regions (CDRs), which CDRs comprise the amino acid sequences of SEQ ID NOs: 1-3, respectively, and wherein said antibody further comprises a light chain comprising three CDRs, which CDRs comprise the amino acid sequences of SEQ ID NOs: 4-6, respectively.

2. The antibody of claim 1, wherein the antibody does not react with a glycopeptide of formula (4) (SEQ ID NO: 16)

[Chemical formula 4]

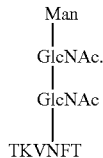
(4)

3. The antibody of claim 1, which further reacts with fucosylated α-fetoprotein (AFP).

4. The antibody of claim 1, wherein the antibody reacts, in the presence of 0.025% by mass or less of SDS, with fucosylated α-fetoprotein (AFP) that has been pretreated by a solution comprising 0.03% by mass or more of SDS.

5. The antibody of claim 1, wherein the antibody reacts with fucosylated α-fetoprotein (AFP) which has been pretreated by a solution comprising 2% by mass of SDS and 50 mM of DTT.

6. The antibody of claim 1, wherein the antibody does not react with a non-fucosylated α-fetoprotein (AFP) which has been pretreated by a solution comprising 2% by mass of SDS and 50 mM of DTT.

7. A reagent kit, comprising
a fucosylated α-fetoprotein (AFP)-capturing antibody,
a fucosylated AFP-detecting antibody and
a solid support,
wherein at least one of the fucosylated AFP-capturing antibody and the fucosylated AFP-detecting antibody is the antibody of claim 1.

8. The kit of claim 7, wherein the fucosylated AFP-capturing antibody is the antibody of claim 1.

9. The kit of claim 7, further comprising a pretreatment solution comprising 0.03% by mass or more of SDS.

10. The kit of claim 7, wherein the solid support is particles, a film, a microplate, a microtube or a test tube.

11. A monoclonal antibody, which reacts with a glycopeptide of formula (1) (SEQ ID NO: 13), does not react with a glycopeptide of formula (2) (SEQ ID NO: 14), and does not react with a glycopeptide of formula (3) (SEQ ID NO: 15):

[Chemical formula 1]

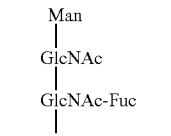
(1)

[Chemical formula 2]

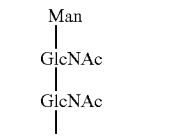
(2)

[Chemical formula 3]

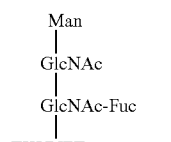
(3)

wherein said antibody comprises a heavy chain comprising three CDRs, which CDRs comprise the amino acid sequences of SEQ ID NOs: 7-9, respectively, and wherein said antibody further comprises a light chain comprising three CDRs, which CDRs comprise the amino acid sequences of SEQ ID NOs: 10-12, respectively.

* * * * *